US010022483B2

(12) United States Patent
Tullis

(10) Patent No.: US 10,022,483 B2
(45) Date of Patent: Jul. 17, 2018

(54) METHOD FOR REMOVAL OF VIRUSES FROM BLOOD BY LECTIN AFFINITY HEMODIALYSIS

(71) Applicant: Aethlon Medical, Inc., San Diego, CA (US)

(72) Inventor: Richard H Tullis, Encinitas, CA (US)

(73) Assignee: Aethlon Medical, Inc., San Diego, CA (US)

( * ) Notice: Subject to any disclaimer, the term of this patent is extended or adjusted under 35 U.S.C. 154(b) by 201 days.

(21) Appl. No.: 14/490,418

(22) Filed: Sep. 18, 2014

(65) Prior Publication Data

US 2015/0093289 A1 Apr. 2, 2015

Related U.S. Application Data

(63) Continuation of application No. 11/756,543, filed on May 31, 2007, which is a continuation of application No. 10/760,810, filed on Jan. 20, 2004, now Pat. No. 7,226,429.

(60) Provisional application No. 60/440,771, filed on Jan. 17, 2003.

(51) Int. Cl.
*A61M 1/34* (2006.01)
*A61L 2/02* (2006.01)

(52) U.S. Cl.
CPC ............ *A61M 1/3486* (2014.02); *A61L 2/02* (2013.01); *A61L 2/022* (2013.01); *A61M 1/3472* (2013.01)

(58) Field of Classification Search
None
See application file for complete search history.

(56) References Cited

U.S. PATENT DOCUMENTS

| | | | |
|---|---|---|---|
| 3,925,152 A | 12/1975 | Porath et al. | |
| 4,215,688 A | 8/1980 | Terman et al. | |
| 4,643,814 A | 2/1987 | Goldstein | |
| 4,668,399 A | 5/1987 | Duggins | |
| 4,714,556 A | 12/1987 | Ambrus et al. | |
| 4,787,974 A | 11/1988 | Ambrus et al. | |
| 5,041,079 A | 8/1991 | Rakashima et al. | |
| 5,061,237 A | 10/1991 | Gessler et al. | |
| 5,106,745 A | 4/1992 | Baron et al. | |
| 5,123,901 A | 6/1992 | Bayne | |
| 5,166,050 A | 11/1992 | Shriver et al. | |
| 5,310,688 A | 5/1994 | Zale et al. | |
| 5,462,853 A | 10/1995 | Steart et al. | |
| 5,462,867 A | 10/1995 | Azad et al. | |
| 5,484,396 A | 1/1996 | Naficy | |
| 5,516,657 A | 5/1996 | Murphy et al. | |
| 5,528,057 A | 6/1996 | Yanagase et al. | |
| 5,637,453 A | 6/1997 | Jehuda-Cohen | |
| 5,667,684 A | 9/1997 | Motomura et al. | |
| 5,942,234 A | 8/1999 | Ralston et al. | |
| 6,071,412 A | 6/2000 | Ambrus et al. | |
| 6,117,100 A | 9/2000 | Powers et al. | |
| 6,159,174 A | 12/2000 | Oldham et al. | |
| 6,165,710 A | 12/2000 | Robinson | |
| 6,174,299 B1 | 1/2001 | Pollard et al. | |
| 6,274,148 B1 | 8/2001 | Ralston et al. | |
| 6,521,423 B1 | 2/2003 | Houghton et al. | |
| 6,528,057 B1 | 3/2003 | Ambrus et al. | |
| 6,562,784 B1 | 5/2003 | Thiel et al. | |
| 6,858,146 B1 | 2/2005 | Myers et al. | |
| 6,951,646 B1 | 10/2005 | Reiter et al. | |
| 7,105,303 B2 | 9/2006 | Ralston et al. | |
| 7,226,429 B2 | 6/2007 | Tullis | |
| 2001/0006776 A1 | 7/2001 | Wong | |
| 2002/0001600 A1 | 1/2002 | Oldham et al. | |
| 2002/0004048 A1 | 1/2002 | Ralston et al. | |
| 2004/0024343 A1 | 2/2004 | Cantor | |
| 2004/0053224 A1 | 3/2004 | Huang | |
| 2004/0140265 A1 | 7/2004 | Lihme | |
| 2004/0175291 A1 | 9/2004 | Tullis et al. | |
| 2007/0218458 A1 | 9/2007 | Tullis | |
| 2009/0304677 A1 | 12/2009 | Ichim et al. | |

(Continued)

FOREIGN PATENT DOCUMENTS

| | | |
|---|---|---|
| CA | 2453198 | 7/2005 |
| JP | 2001-276181 | 10/2001 |
| WO | WO 9114706 | 10/1991 |

(Continued)

OTHER PUBLICATIONS

Ambrus et al., "Extracorporeal Enzyme Reactors for Depletion of Phenylalanine in Phenylketonuria," *Ann Intern Med*, (1987) vol. 106, Issue (4): pp. 531-537.
Ambrus, et al., "Phenylalanine Depletion for the Management of Phenylketonuria: use of Enzyme Reactors with Immobilized Enzymes," *Science*, (1978) vol. 201, Issue (4358): pp. 837-839.
Amin et al., "Binding of Galanthus Nivalis Lectin to Chlamydia Trachomatis and Inhibition of In Vitro Infection," *APMIS*, (1995) vol. 103, Issue (10): pp. 714-720.
Anthone, et al., "Treatment of Aluminum Overload Using a Cartridge with Immobilized Desferrioxamine," *J. Am. Soc. Nephrol.*, (1995) vol. 6, Issue (4): pp. 1271-1277.
Azuma et al., Alteration of sugar chains on a-acid glycoprotein 1 secreted following cytokine stimulation of HuH-7 cells in vitro, 2000, Clinica Chimica Acta, vol. 294, pp. 93-103.
Bartoszewicz et al., "Prominent 85-kDa oligomannosidic glycoproteins of rat brain are signal regulatory proteins and include the SHP substrate-1 for tyrosine phosphatases," J Neurochem (1999) 72(4):1688-1693.

(Continued)

*Primary Examiner* — Benjamin P Blumel
(74) *Attorney, Agent, or Firm* — Knobbe Martens Olson & Bear LLP

(57) ABSTRACT

The present invention relates to a method for using lectins that bind to pathogens having high mannose surface glycoproteins or fragments thereof which contain high mannose glycoproteins, to remove them from infected blood or plasma in an extracorporeal setting. Accordingly, the present invention provides a method for reducing viral load in an individual comprising the steps of obtaining blood or plasma from the individual, passing the blood or plasma through a porous hollow fiber membrane wherein lectin molecules are immobilized within the porous exterior portion of the membrane, collecting pass-through blood or plasma and reinfusing the pass-through blood or plasma into the individual.

5 Claims, 4 Drawing Sheets

(56) References Cited

U.S. PATENT DOCUMENTS

| | | | |
|---|---|---|---|
| 2010/0267006 | A1 | 10/2010 | Namba |
| 2016/0000987 | A1* | 1/2016 | Tullis .................. A61M 1/3679 210/638 |

FOREIGN PATENT DOCUMENTS

| | | |
|---|---|---|
| WO | WO 9740861 | 11/1997 |
| WO | WO 9748483 | 12/1997 |
| WO | WO 00/12103 | 3/2000 |
| WO | WO 0012103 | 3/2000 |
| WO | WO 02/38032 A2 | 5/2002 |
| WO | WO 02053251 | 7/2002 |
| WO | WO 2004/064608 | 8/2004 |
| WO | WO 2007/103572 | 9/2007 |
| WO | WO 2009/023332 | 2/2009 |
| WO | WO 2009/086203 | 7/2009 |
| WO | WO 2009/149179 | 12/2009 |
| WO | WO 2010/033514 | 3/2010 |

OTHER PUBLICATIONS

Batinic, et al., "The V3 Region of the Envelope Glycoprotein of Human Immunodeficiency Virus Type 1 Binds Sulfated Polysaccharides and CD4-derived Synthetic Peptides," *Journal of Biological Chemistry*, (1992) vol. 267, Issue (10): pp. 6664-6671.

Boyd, et al., "Discovery of Cyanovirin-N, a Novel Human Immunodeficiency Virus-inactivating Protein that Binds Viral Surface Envelope Glycoprotein gp120: Potential Applications to Microbicide Development," *Antimicrob. Agents Chemother.*, (1997) vol. 41, Issue (7) pp. 1521-1530.

Chapman, et al., "Binding of Serum Ferritin to Concanavalin A in Patients with Iron Overload and with Chronic Liver Disease," *J Clin Pathol.*, (1982) vol. 35, Issue 5: pp. 481-486.

Chapman, et al.., "Serum Ferritin and Binding of Serum Ferritin to Concanavalin A as a Tumor Marker in Patients with Primary Liver Cell Cancer and Chronic Liver Disease," *Dig. Dis. Sci.*, (1982) vol. 27, Issue (2): pp. 111-116.

Chen, et al., "Quantitative Detection of Hepatitis B Virus DNA in Human Sera by 'Branched-DNA Signal Amplification'," *Journal of Virological Methods*, (1995) vol. 53, Issue (1): pp. 131-137.

Chervenak, et al., "Calorimetric Analysis of the Binding of Lectins with Overlapping Carbohydrate-binding Ligand Specificities," *Biochemistry*, (1995) vol. 34, Issue (16): pp. 5685-5695.

Clarke et al., "The Interaction of Concanavalin A with Blood-Group-Subtance Glycoproteins from Human Secretions," *Biochem. J.*, (1971) vol. 121: pp. 811-816.

De Clercq, et al., "Current Lead Natural Products for the Chemotherapy of Human Immunodeficiency Virus (HIV) Infection," *Med. Res. Rev.*, (2000) vol. 20, Issue (5): pp. 323-349.

Deeks, et al., "Variance of Plasma Human Immunodeficiency Virus Type 1 RNA Levels Measured by Branched DNA Within and Between Days," *The Journal of Infectious Diseases*, (1997) vol. 176, Issue (2): pp. 514-517.

Finn et al., Cancer Vaccines: Between the Idea and the Reality, Nature Reviews Immunology, Aug. 2003, vol. 3, pp. 630-641.

Gilljam, et al., "Envelope Glycoproteins of HIV-1, HIV-2, and SIV Purified with Galanthus Nivalis Agglutinin Induce Strong Immune Responses," *AIDS Res. Hum. Retroviruses*, (1993) vol. 9, Issue (5): pp. 431-438.

Hammar et al., "Lectin Effects on HIV-1 Infectivity," Annals New York Academy of Sciences, (1994) vol. 724: pp. 166-169.

Hammar, et al., "Lectin-mediated Effects on HIV Type 1 Infection In Vitro," *AIDS Res. Hum. Retroviruses*, (1995) vol. 11, Issue (1): pp. 87-95.

Hinkula, et al., "Enzyme Immunoassay (ELISA) for the Evaluation of Antibodies Directed to the CD4 Receptor-binding Site of the HIV gp120 Molecule," *J. Immunol. Methods*, (1994) vol. 175, Issue (1): pp. 37-46.

Kaku, et al., "Carbohydrate-binding Specificity of the Daffodil (*Narcissus pseudonarcissus*) and Amaryllis (*Hippeastrum hybr.*) Bulb Lectins," *Arch. Biochem. Biophys.*, (1990) vol. 279, Issue (2): pp. 298-304.

Kalghatgi, et al., "Multitubular Reactors with Immobilized L-phenylalanine Ammonia-lyase for Use in Extracorporeal Shunts," *Res. Commun. Chem. Pathol. Pharmacol.*, (1980) vol. 27, Issue (3): pp. 551-561.

Kalraiya, et al., "Isolatin of a Glycoprotein Responsible for the Enhanced Concanavalin A Agglutinability of Erythrocytes in Yoshida-ascites-sarcoma-bearing Rats: The Mechanism of Paraneoplastic Syndromes," *Biochm. J.*, (1993) vol. 292: pp. 163-170.

Khaitov, et al., "Meditsina," *Immunology*, Moscow, (2002): pp. 80, 352-353.

Krzeslak et al., "Glycoproteins present in the fraction of chromatin proteins loosely bound to DNA from hamster, chicken and frog liver cells," Gen Physiol Biophys (2001) 20:145-155.

Partial English abstract of Khaitov, et al., "Meditsina," Immunology, Moscow, (2002): pp. 80, 352-353.

Leuven et al., "Mannose-speciifc Lectins Bind Alpha-2-macroglobulin and an Unknown Protein from Human Plasma," *Protein Science*, (1993) vol. 2: pp. 255-263.

Lopukhin, et al., "Immunoperfusion of Individual Proteins and HIV-1 Virions," *Vestnik Akademii Meditsinskikh Nauk SSSR*, (1991) vol. 11: pp. 60-63.

Partial English abstract of Lopukhin, et al., "Immunoperfusion of Individual Proteins and HIV-1 Virions," *Vestnik Akademii Meditsinskikh Nauk SSSR*, (1991) vol. 11: pp. 60-63.

Mahmood, et al., "An ELISA Utilizing Immobilised Snowdrop Lectin GNA for the Detection of Envelope Glycoproteins of HIV and SIV," *J. Immunol. Methods*, (1992) vol. 151, Issue (1-2): pp. 9-13.

Nicholls et al., Sialic acid receptor detection in the human respiratory tract: evidence for widespread distribution of potential binding sites for human and avian influenza viruses, 2007, Respiratory Research, vol. 8, No. 73, pp. 1-10.

Raz et al., Isolation of Plasma Memebrane Fragments and Vesicles from Ascites Fluid of Lymphoma-Bearing Mice and Their Possible Role in the Escape Mechanism of Tumors from Host Immune Rejection, Cancer Immunology Immunotherapy, 1978, vol. 4, pp. 53-59.

Sanders et al., "The Mannose-Dependent Epitope for Neutralizing Antibody 2G12 on Human Immunodeficiency Virus Type 1 Glycoprotein gp 120," *Journal of Virology*, (2002) vol. 76, Issue (14): pp. 7293-7305.

Savage et al., "T Cell-B cell interaction: autoreactive T cells recognize B cells through a terminal mannose-containing superantigen-like glycoprotein," Cell Immunol (1993) 146:11-27.

Sherman, et al., "Quantitative Evaluation of Hepatitis C Virus RNA in Patients with Concurrent Human Immunodeficiency Virus Infections," *Journal of Clinical Microbiology*, (1993) vol. 31, Issue (10): pp. 2679-2682.

Shibuya et al., "One-Step Purification of Murine IgM and Human alpha2-Macroglobulin by Affinity Chromatography on Immobilized Snowdrop Bulb Lectin," Archives of Biochemistry and Biophysics, (1988) vol. 267, Issue (2): pp. 676-680.

Sibille, et al., "Comparison of Serological Tests for the Diagnosis of Feline Immunodeficiency Virus Infection of Cats," *Vet. Microbiol.*, (1995) vol. 45, Issue (2-3): pp. 259-267.

Sinkora et al., "Binding of the galanthus nivalis agglutinin to thymocytes reveals alterations in surface flycosylation during T-cell development," Scand J Immunol (2002) 55:196-203.

Sottrup-Jensen, et al., "Alpha-Macrogloubulins: Structure, Shape, and Mechanism of Proteinase Complex Formation," *The Journal of Biological Chemistry*, (1989) vol. 264, Issue 20: pp. 11539-11542.

Urdea, et al., "Direct and Quantitative Detection of HIV-1 RNA in Human Plasma with a Branched DNA Signal Amplification Assay," *AIDS*, (1993) vol. 7, Suppl. 2: pp. S11-S14.

Zimmerman, et al., "Generation of a Human Monoclonal Antibody to Hepatitis C Virus, JRA1 by Activation of Peripheral Blood Lymphocytes and Hypo-osmolar Electrofusion," *Human Antibodies and Hybridomas*, (1995) vol. 6, Issue (2): pp. 77-80.

(56) References Cited

OTHER PUBLICATIONS

International Search Report and Written Opinion dated Jul. 7, 2006 for PCT/US04/01559, filed Jan. 20, 2004.
International Search Report dated Feb. 24, 2009 for PCT/US2008/063946, filed May 16, 2008.

\* cited by examiner

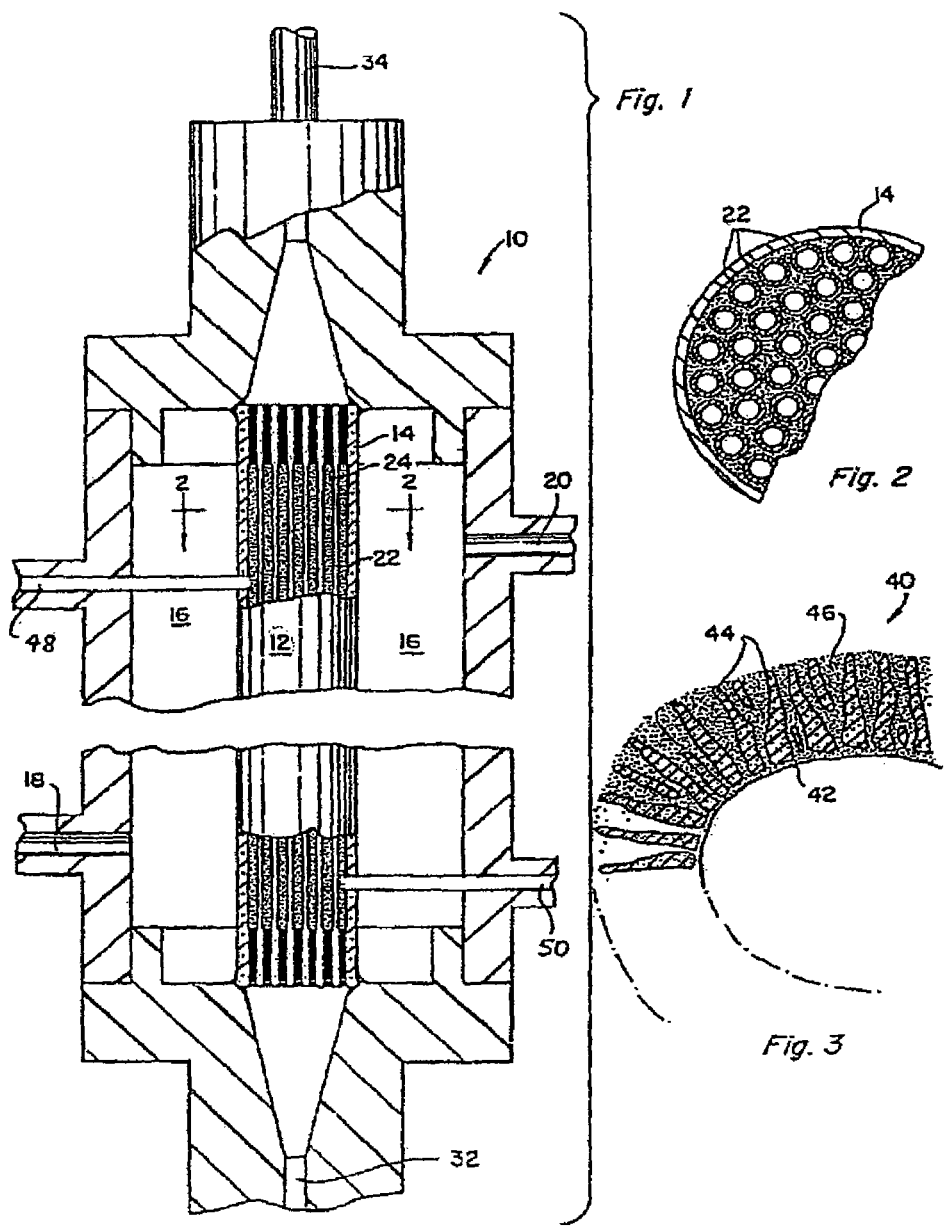

METHOD FOR REMOVAL OF VIRUSES FROM BLOOD BY LECTIN AFFINITY HEMODIALYSIS

This application is a continuation of U.S. patent application Ser. No. 10/760,810, filed Jan. 20, 2004, which claims the benefit under 35 USC § 119(e) of U.S. Provisional Application No. 60/440,771, filed Jan. 17, 2003, the disclosures of which are incorporated herein by reference.

FIELD OF THE INVENTION

The present invention relates to the field of therapeutic methodologies for treating viral infections.

BACKGROUND OF THE INVENTION

A large number of viruses have been described which are pathogenic for humans. Among these viruses are many for which neither drugs nor vaccines are available. In cases where drug treatments are available, the occurrence of resistant mutations and drug side effects often limit the effectiveness of therapy. Examples of such viruses include Hepatitis C and human immunodeficiency virus (HIV).

HIV is the etiological agent of acquired immunodeficiency syndrome (AIDS). It infects selected cells of the immune system thereby compromising the infected individual's immune response. It is estimated that there are over 1 million HIV infected individuals in the United States and over 13 million worldwide. The clinical course of HIV infection typically consists of a prolonged asymptomatic state, followed by a depletion of T4 lymphocytes making the individual susceptible to opportunistic infections and neoplasms.

HIV-1 replication occurs predominantly in CD4+ lymphocytes, the majority of which are located in lymphoid organs, such as peripheral lymph nodes and spleen. HIV-1 can also be found in macrophages and macrophage-like cells, such as microglia in the central nervous system (Cohen et al. Immunol Rev 159: 31-48, 1997).

Plasma HIV-1 levels and presence of HIV-1 infected lymphocytes in peripheral blood strongly correlate with the clinical status of HIV-1 infected patients (Ferre et al. J Acquir Immune Defic Syndr Hum Retrovirol 10(Suppl 2): S51-56, 1995; O'Brien et al. N Engl J Med 334(7): 426-431, 1996). The half-life of circulating virions is 6 hours, while the half-life of HIV-1 infected cells in peripheral blood is 1.6 days. Greater than $10^{10}$ virions may be released into the circulation each day (Ho et al. J Biol Regul Homeost Agents 9(3): 76-77, 1995; Ho et al. Nature 373(6510): 123-126, 1995; Wei et al. Nature 373(6510): 117-122, 1995). The ability of the host immune system to keep HIV infection in check, and limit clinical symptoms, is directly proportional to the viral burden. Anti-retroviral therapies, nucleoside analogues, non-nucleoside reverse transcriptase inhibitors, and protease inhibitors, aim to reduce the viral burden so that the immune system can control or clear residual infection (Fauci, Harrisons Principles of Internal Medicine: 1791-1856, 1998).

HIV infection is mediated by gp120, which binds to CD4 as well as to a surface chemokine receptor. Inside the cell the virion is uncoated and the viral RNA is reverse transcribed into double-stranded DNA. Proviral DNA enters the cell nucleus, integrates into the host genome and is transcribed into viral RNAs, which are translated into viral proteins. Mature virions are assembled and released from the cell by budding. (Fauci et al. Ann Intern Med 124(7): 654-663, 1996). A dying cell may also release all its contents including intact virions, and fragments thereof into the blood. Thus, circulating blood of HIV-infected individuals contains intact virions, and viral proteins, in particular toxic viral surface proteins.

The hallmark of AIDS is the gradual loss of CD4+ T cells, which ultimately leaves the immune system unable to defend against opportunistic infections. While the mechanism through which HIV causes AIDS is imperfectly understood, the clinical data suggest that in addition to the loss of infected T-cells, a large number of uninfected T-cells are dying and that HIV derived envelope proteins appear to be intimately involved.

The major HIV envelope glycoprotein gp120 has been shown to have profound biological effects in vitro. Gp120 causes CD4+ T cells to undergo apoptosis and binding of gp120 to CD4+ cells in the presence of anti-envelope antibodies and complement opsoninizes the cells, targeting them for clearance. The combined effect is the destruction of uninfected immune cells. In addition, HIV envelope proteins have been implicated in HIV related hyper-gammaglobulinemia. In AIDS patients, gp120 levels have been measured at an average of 29 ng/ml which is orders of magnitude higher than the concentration of the virus.

Currently there is no cure for HIV infection. Reverse transcriptase and protease inhibitors have been approved for the treatment of HIV. Typical treatment regimes use combinations of approved drugs and are termed HAART (highly active antiretroviral therapy). While more than 16 drugs and drug combinations have been approved by the FDA for treating HIV infection, the emergence of drug resistant mutants and the presence of the untreatable virus reservoirs (e.g. in memory T cells) has limited their usefulness. Unfortunately, no effective HIV vaccine has been forthcoming due, in part, to the rapid mutation of the HIV genome and the inaccessibility of immunogenic epitopes of viral proteins. Thus there is an urgent need for new treatments.

Extracorporeal treatments provide a therapeutic modality which may be used to treat systemic disease. Extracorporeal perfusion of plasma over protein A, plasmapheresis and lymphapheresis have all been used as immunomodulatory treatments for HIV infection, and the thrombocytopenia resulting from it (Kiprov et al. Curr Stud Hematol Blood Transfus 57: 184-197, 1990; Mittelman et al. Semin Hematol 26(2 Suppl 1): 15-18, 1989; Snyder et al. Semin Hematol 26(2 Suppl 1): 31-41, 1989; Snyder et al. Aids 5(10): 1257-1260, 1991). These therapies are all proposed to work by removing immune complexes and other humoral mediators, which are generated during HIV infection. They do not directly remove HIV virus. Extracorporeal photopheresis has been tested in preliminary trials as a mechanism to limit viral replication (Bisaccia et al. J Acquir Immune Defic Syndr 6(4): 386-392, 1993; Bisaccia et al. Ann Intern Med 113(4): 270-275, 1990). However, none of these treatments effectively remove both virus and viral proteins.

Chromatographic techniques for the removal of HIV from blood products have been proposed. In 1997, Motomura et al., proposed salts of a sulfonated porous ion exchanger for removing HIV and related substances from body fluids (U.S. Pat. No. 5,667,684). Takashima and coworkers (U.S. Pat. No. 5,041,079) provide ion exchange agents comprising a solid substance with a weakly acidic or weakly alkaline surface for extracorporeal removal of HIV from the body fluids of a patient. Both are similar to the work of Porath and Janson (U.S. Pat. No. 3,925,152) who described a method of separating a mixture of charged colloidal particles, e.g. virus variants by passing the mixture over an adsorbent constituted of an insoluble, organic polymer containing amphoteric substituents composed of both basic nitrogen-containing groups and acidic carboxylate or sulphonate groups (U.S. Pat. No. 3,925,152). However, none of these chromatographic materials are selective for viruses and will clearly remove many other essential substances. Thus they are not useful for in vivo blood purification.

Immunosorptive techniques have also been proposed for the treatment of viral infections. In 1980, Terman et al. described a plasmapheresis apparatus for the extracorporeal treatment of disease including a device having an immunoadsorbent fixed on a large surface area spiral membrane to remove disease agents (U.S. Pat. No. 4,215,688). The device envisioned no method for directly treating blood and required the presence of an immunologically reactive toxic agent. In 1987 and 1988, Ambrus and Horvath described a blood purification system based on antibody or antigen capture matrices incorporated onto the outside surface of an asymmetric, toxin permeable membrane (U.S. Pat. Nos. 4,714,556; 4,787,974), however, no examples of pathogen removal were given therein. In 1991, Lopukhin et al. reported that rabbit antisera raised against HIV proteins, when coupled to Sepharose 4B or silica, could be used for extracorporeal removal of HIV proteins from the blood of rabbits which had been injected with recombinant HIV proteins (Lopukhin et al. Vestn Akad Med Nauk SSSR 11: 60-63, 1991). However, this strategy was inefficient as it required extracorporeal absorption of blood and did not provide for a mechanism to remove free HIV viral particles from the blood (Lopukhin et al., 1991, supra). U.S. Pat. No. 6,528,057 describes the removal of virus and viral nucleic acids using antibodies and antisense DNA.

Lectins are proteins that bind selectively to polysaccharides and glycoproteins and are widely distributed in plants and animals. Although many are insufficiently specific to be useful, it has recently been found that certain lectins are highly selective for enveloped viruses (De Clercq. et al Med Res Rev 20(5): 323-349, 2000). Among lectins which have this property are those derived from *Galanthus nivalis* in the form of *Galanthus nivalis* agglutinin ("GNA"), *Narcissus pseudonarcissus* in the form of *Narcissus pseudonarcissus* agglutinin ("NPA") and a lectin derived from blue green algae *Nostoc ellipsosporum* called "cyanovirin" (Boyd et al. Antimicrob Agents Chemother 41(7): 1521-1530, 1997; Hammar et al. Ann N Y Acad Sci 724: 166-169, 1994; Kaku et al. Arch Biochem Biophys 279(2): 298-304, 1990). GNA is non-toxic and sufficiently safe that it has been incorporated into genetically engineered rice and potatoes (Bell et al. Transgenic Res 10(1): 35-42, 2001; Rao et al. Plant J 15(4): 469-477, 1998). These lectins bind to glycoproteins having a high mannose content such as found in HIV surface proteins (Chervenak et al. Biochemistry 34(16): 5685-5695, 1995). GNA has been employed in ELISA to assay HIV gp120 in human plasma (Hinkula et al. J Immunol Methods 175(1): 37-46, 1994; Mahmood et al. J Immunol Methods 151(1-2): 9-13, 1992; Sibille et al. Vet Microbiol 45(2-3): 259-267, 1995) and feline immunodeficiency virus (FIV) envelope protein in serum (Sibille et al. Vet Microbiol 45(2-3): 259-267, 1995). While GNA binds to envelope glycoproteins from HIV (types 1 and 2), simian immunodeficiency virus (SIV) (Gilljam et al. AIDS Res Hum Retroviruses 9(5): 431-438, 1993) and inhibits the growth of pathogens in culture, (Amin et al. Apmis 103(10): 714-720, 1995; Hammar et al. AIDS Res Hum Retroviruses 11(1): 87-95, 1995) such in vitro studies do not reflect the complex, proteinacious milieu found in HIV infected blood samples. It is therefore not known if lectins capable of binding high mannose glycoproteins in vitro would be able to bind such molecules in HIV infected blood samples. On the contrary, it is generally considered that the high concentrations of antibodies to gp120 typically present in individuals infected with HIV would sequester the high mannose glycoprotein sites to which lectins such as GNA bind.

Accordingly, although lectins are known to bind viral envelope glycoproteins, no previous technologies have been developed using lectins to directly adsorb HIV or other enveloped viruses from the blood using in vivo dialysis or plasmapheresis. Therefore, there is an ongoing need for novel therapeutic approaches to the treatment of HIV and other viral infections. In particular, there is a need for the development of novel approaches to reduce viral load so as to increase the effectiveness of other treatments and/or the immune response.

SUMMARY OF THE INVENTION

The present invention relates to a method for using lectins that bind to pathogens having high mannose glycoproteins or fragments thereof to remove them from infected blood or plasma in an extracorporeal setting. Accordingly, the present invention provides a method for reducing viral load in an individual comprising the steps of obtaining blood or plasma from the individual, passing the blood or plasma through a porous hollow fiber membrane wherein lectin molecules are immobilized within the porous exterior portion of the membrane, collecting pass-through blood or plasma and reinfusing the pass-through blood or plasma into the individual.

Passage of the blood through the hollow fibers having immobilized lectin causes the virions and fragments thereof which contain high mannose glycoproteins to bind to the lectins, thereby reducing the viral load in the effluent. In one embodiment, this invention uses lectins that bind viral envelope proteins of many subtypes of HIV types 1 and 2 and SIV. The method of the present invention reduces the number of virions in the blood and rapidly and effectively reduces the levels of viral surface proteins in infected blood which may be toxic. It will be apparent to those skilled in the art that the method will assist in the clearance of other infections, frequently occurring simultaneously with HIV-1, such as hepatitis C virus (HCV) (Fauci et al., 1998, supra).

Thus, an object of the invention is to provide a method for reducing the viral load in the blood of an individual infected with a virus. In one embodiment, virions or protein fragments thereof or combinations thereof are removed from the blood of an individual infected with a virus.

Another object of the present invention is to provide a method for reducing the viral load in the blood by extracorporeal circulation of blood through hollow fibers containing immobilized lectins having affinity for viral high mannose glycoproteins.

Another object of the present invention is to provide an apparatus comprising hollow fibers, wherein the exterior surface of the fibers is in close proximity with immobilized lectins having specific affinity for high mannose glycoproteins in the virus or other pathogen.

BRIEF DESCRIPTION OF THE DRAWINGS

FIG. 1 is a schematic illustration of a longitudinal cross section of an affinity cartridge.

FIG. 2 is a schematic illustration of a horizontal cross section at plane 2 in FIG. 1.

FIG. 3 is an illustration of a channel from FIG. 2. A hollow fiber membrane structure 40 is composed of a tubular section comprising a relatively tight ultrafiltration membrane 42 and relatively porous exterior portion 44 in which may be immobilized affinity molecules 46, such as lectins.

FIG. 6A is a graphical representation of a plasmapheresis exponential curve where $R^2 0.90$ (excluding one point at 22 hours). FIG. 6B is a graphical representation of a log plot of initial removal rate, where half time ~0.9 hours. Conditions Masterflex pump with #14 silicon tubing (1.1 ml/min). Plasma sample 3 ml initial volume (100,000 copies per ml (CPM) BBI ER8-03030-0002 native HIV). Aliquot volume was 250 ul plasma for RNA isolation. Realtime RTPCR with Sybr green tracking dye. Thermocycling 95, 60, 72, 83° C. (15, 30, 60 sec, read 6 sec). Ct calculated from the primary curve at T=20.

DETAILED DESCRIPTION OF THE INVENTION

Figure 4:
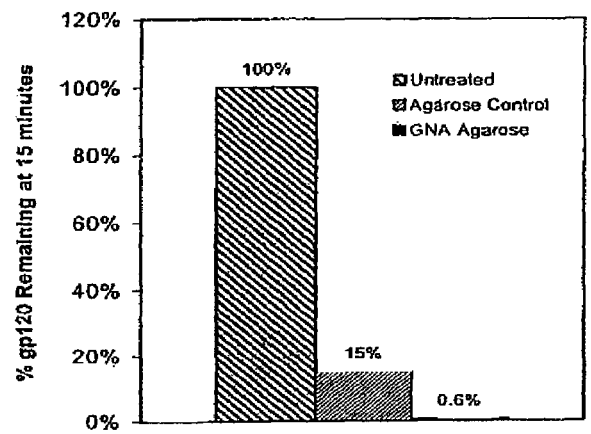
FIG. 4 is a graphical representation of the removal of gp120 from HIV loaded physiological saline. Initial gp120 was 500 ng/ml in PBS (1.6 ml/run). Gp120 was recirculated over a column containing 0.2 ml GNA agarose vs Sepharose 4B control at 0.5-0.58 ml/min and room temperature.

The term "viral load" as used herein for the purpose of specification and claims refers to the amount of viral particles or toxic fragments thereof in a biological fluid, such as blood or plasma. Viral load is accordingly related to the number of virus particles in the body. Viral load can therefore be a measure of any of a variety of indicators of the presence of a virus, such as viral copy number per unit of blood or plasma or units of viral proteins or fragments thereof per unit of blood or plasma.

The term "high mannose glycoprotein" as used herein for the purpose of the specification and claims refers to glycoproteins having mannose-mannose linkages in the form of α-1->3 or α-1->6 mannose-mannose linkages. Some examples of such lectins include GNA, NPA, cyanovirin and Conconavalin A (ConA).

The present invention relates to a method for using lectins to remove pathogenic organisms and fragments thereof from infected blood or plasma in an extracorporeal setting. Accordingly, the present invention provides a method for reducing viral load in an individual comprising the steps of obtaining blood or plasma from the individual, passing the blood or plasma through a porous hollow fiber membrane wherein lectin molecules which bind to high mannose glycoproteins are immobilized within the porous exterior portion of the membrane, collecting pass-through blood or plasma, and reinfusing the pass-through blood or plasma into the individual.

In a preferred embodiment, the method of the present invention is carried out by using an affinity cartridge using the device illustrated in FIG. 1. Devices of this general type are disclosed in U.S. Pat. Nos. 4,714,556, 4,787,974 and 6,528,057, the disclosures of which are incorporated herein by reference. In this device, blood is passed through the lumen of a hollow fiber ultrafiltration membrane that is in intimate contact, on the non-blood wetted side of the membrane, with immobilized lectins, which form a means to accept and immobilize viruses and toxic and/or infectious fragments thereof. Thus, the device retains intact virions and viral glycoproteins bound by lectin while allowing other components to pass through the lumen.

HIV is the prototypic virus for which this invention is described, but the invention can be adapted to the removal of any blood-borne viruses. The device, described in detail in FIGS. 1-3 includes multiple channels of hollow fiber ultrafiltration membrane that forms a filtration chamber. An inlet port and an effluent port are in communication with the filtration chamber. The ultrafiltration membrane is preferably an anisotropic membrane with the tight or retention side facing the bloodstream. The membrane is conveniently formed of any number of polymers known to the art, for example, polysulfone, polyethersulfone, polyamides, polyimides, cellulose acetate, and polyacrylamide. Preferably, the membrane has pores 200-500 nm in diameter, which will allow passage of intact viruses and viral particles and fragments (e.g., HIV virions of 110 nm diameter), but not most blood cells (red blood cells 2,000 nm diameter, lymphocytes 7,000-12,000 am diameter, macrophages 10,000-18,000 nm diameter). A diagram of the device is shown in FIG. 1. The device comprises a cartridge 10 comprising a blood-processing chamber 12 formed of interior glass wall 14. Around chamber 12 is an optional exterior chamber 16. A temperature controlling fluid can be circulated into chamber 16 through port 18 and out of port 20. The device includes an inlet port 32 for the blood and an outlet port 34 for the effluent. The device also provides one or more ports 48 and 50, for accessing the extrachannel space in the cartridge. As shown in FIGS. 1 and 2, chamber 12 contains a plurality of ultrafiltration membranes 22. These membranes preferably have a 0.3 mm inside diameter and 0.5 min outside diameter. FIG. 3 is a cross sectional representation of a channel 22 and shows the anisotropic nature of the membrane. As shown in FIG. 3, a hollow fiber membrane structure 40 is composed of a single polymeric material which is formed into a tubular section comprising a relatively tight ultrafiltration membrane 42 and relatively porous exterior portion 44 in which may be immobilized lectins 46. During the operation of the device, a solution containing the lectins is loaded on to the device through port 48. The lectins are allowed to immobilize to the exterior 22 of the membrane in FIG. 2. Unbound lectins can be collected from port 50 by washing with saline or other solutions.

For the method of the present invention, blood having viral particles and/or fragments thereof is withdrawn from a patient and contacted with an ultrafiltration membrane. In one preferred embodiment, the blood is separated into its plasma and cellular components. The plasma is then contacted with the lectins to remove the viral particles or fragments thereof by binding between viral high mannose glycoproteins and lectins. The plasma can then be recombined with the cellular components and returned to the patient. Alternatively, the cellular components may be returned to the patient separately. The treatment can be repeated periodically until a desired response has been achieved. For example, the treatment can be carried out for 4 hours once a week.

The technology to immobilize enzymes, chelators, and antibodies in dialysis-like cartridges has been developed (Ambrus et al. Science 201(4358): 837-839, 1978; Ambrus et al. Ann Intern Med 106(4): 531-537, 1987; Kalghatgi et al. Res Commun Chem Pathol Pharmacol 27(3): 551-561, 1980) and is incorporated herein by reference. These cartridges can be directly perfused with blood from patients through direct venous access, and returned to the patients without further manipulations. Alternatively, blood can be separated into plasma and cellular components by standard techniques. The cellular components may be combined with the plasma before reinfusing or the cellular components can be reinfused separately. Viral load can be assessed in the effluent from the cartridge by standard techniques such as ELISA and nucleic acid amplification and detection techniques. Prototypic cartridges have been used to metabolize excess phenylalanine (Kalghatgi et al., 1980, supra; Ambrus, 1978, supra) or to remove excess aluminum from patients' blood (Anthone at al. J Amer Soc Nephrol 6: 1271-1277, 1995). An illustration of preparing proteins for immobilization to the hollow fibers for the method of the present invention is presented in U.S. Pat. Nos. 4,714,556 and 4,787,974, 5,528,057.

For binding of lectins to the ultrafiltration membrane, the polymers of the ultrafiltration membrane are first activated, i.e., made susceptible for combining chemically with proteins, by using processes known in the art. Any number of different polymers can be used. To obtain a reactive polyacrylic acid polymer, for example, carbodiimides can be used (Valuev et al., 1998, *Biomaterials*, 19:41-3). Once the polymer has been activated, the lectins can be attached directly or via a linker to form in either case an affinity matrix. Suitable linkers include, but are not limited to, avidin, strepavidin, biotin, protein A, and protein G. The lectins may also be directly bound to the polymer of the ultrafiltration membrane using coupling agents such as bifunctional reagents, or may be indirectly bound. In a preferred embodiment, GNA covalently coupled to agarose can be used to form an affinity matrix.

The following examples are presented to illustrate this invention and are not intended to be restrictive.

Example 1

This Example demonstrates the preparation of an affinity matrix using GNA covalently coupled to Agarose using Cyanogen Bromide. Cyanogen bromide (CNBr) activated agarose was used for direct coupling essentially according to Cuatrecasas, et al (Cuatracasas et al. Proc Natl Acad Sci USA 61(2): 636-643, 1968). In brief, 1 ml of GNA at a concentration of 10 mg/ml in 0.1M NaHCO$_3$ pH 9.5 is added to 1 ml CNBr activated agarose (Sigma, St. Louis, Mo.) and allowed to react overnight in the cold. When the reaction is complete, unreacted materials are aspirated and the lectin coupled agarose washed extensively with sterile cold PBS. The lectin agarose affinity matrix is then stored cold until ready for use. Alternatively, GNA agarose is available commercially from Vector Labs (Burlingame, Calif.)

Example 2

This Example demonstrates preparation of the lectin affinity matrix using GNA covalently coupled to glass beads via Schiff's base and reduction with cyanoborohydride. The silica lectin affinity matrix was prepared by a modification of the method of Hermanson (Hermanson, Bioconjugate Techniques: 785, 1996). GNA lectin was dissolved to a final protein concentration of 10 mg/ml in 0.1M sodium borate pH 9.5 and added to aldehyde derivatized silica glass beads (BioConnexant, Austin Tex.). The reaction is most efficient at alkaline pH but will go at pH 7-9 and is normally done at a 2-4 fold excess of GNA over coupling sites. To this mixture was added 10 µl 5M NaCNBH$_3$ in 1N NaOH (Aldrich, St Louis, Mo.) per ml of coupling reaction and the mixture allowed to react for 2 hours at room temperature. At the end of the reaction, remaining unreacted aldehyde on the glass surfaces are capped with 20 µl 3M ethanolamine pH 9.5 per ml of reaction. After 15 minutes at room temperature, the reaction solution was decanted and the unbound proteins and reagents removed by washing extensively in PBS. The matrix was the stored in the refrigerator until ready for use.

Example 3

This Example demonstrates preparation of GNA covalently coupled to aminocelite using glutaraldehyde. Aminocelite was prepared by reaction of celite (silicate containing diatomaceous earth) by overnight reaction in a 5% aqueous solution of aminopropyl triethoxysilane. The aminated celite was washed free of excess reagent with water and ethanol and dried overnight to yield an off white powder. One gram of the powder was then suspended in 5 ml 5% glutaraldehyde (Sigma) for 30 minutes. Excess glutaraldehyde was then removed by filtration and washing with water until no detectable aldehyde remained in the wash using Schiff's reagent. The filter cake was then resuspended in 5 ml of Sigma borohydride coupling buffer containing 2-3 mg/ml GNA and the reaction allowed to proceed overnight at room temperature. At the end of the reaction, unreacted GNA was washed off and the unreacted aldehyde aminated with ethanolamine as described. After final washing in sterile PBS, the material was stored cold until ready for use.

Example 4

This Example demonstrates the preparation of an exemplary lectin plasmapheresis device. Small volume filter cartridges (Glen Research, Silverton, Va.) were prepared containing 0.2 ml lectin resin, sealed and equilibrated with 5-10 column volumes sterile PBS. The cartridges were used immediately.

Example 5

This Example demonstrates preparation of a GNA lectin affinity hemodialysis device. The viral Hemopurifier was made by pumping a slurry of particulate immobilized GNA on agarose beads or celite in sterile PBS buffer into the outside compartment of a hollow-fiber dialysis column using a syringe. For blood samples up to 15 mls, Microkros polyethersulfone hollow-fiber dialysis cartridge equipped with Luer fittings (200μ ID×240μ OD, pore diameter 200-500 nm, ~0.5 ml internal volume) obtained from Spectrum Labs (Rancho Dominguez, Calif.) were used. Cartridges containing the affinity resin were equilibrated with 5-10 column volumes sterile PBS.

Example 6

This Example demonstrates removal of HIV gp120 from physiological saline using an affinity plasmapheresis device. The plasmapheresis device described in Example 4 was equilibrated with 5-10 column volumes sterile PBS. A sample ~1.5 ml containing gp120 (typically 500 ng/ml) was circulated over the column at a flow rate of 0.5-0.6 ml/min at room temperature. The circulating solution was tested at various time intervals for the presence of gp120 and gp120 immune complexes where appropriate.

Quantitative ELISA assays for HIV-1 gp120 were performed using a modification of the method of Weiler (Weiler et al. J Viral Methods 32(2-3): 287-301, 1991). GNA/NPA plates were prepared on Greiner C bottom plates by adding 100 ul protein (1-100 μg/ml each of GNA and NPA in PBS) to each well and incubating 2 hours at 37° C. The plates were then washed in PBST (PBS containing 0.01% Tween 20) and blocked in Casein blocking buffer for 1 hour at 37° C. Plates not used immediately were stored for up to 2 weeks at 4° C.

For detection of free gp120, 100 μl, samples of test solutions were incubated for 1-2 hours at 37° C. After capture, plates were washed in PBS and 100 μl of the appropriate horse radish peroxidase (HRP) labeled anti-gp120 antibody (1:2500 in blocking buffer) was added. After incubation for 1 hour at 37° C. the antiserum was aspirated and the plates washed 4×300 ul PBSTA and the bound HRP detected with stabilized tetramethylbenzidine (TMB) substrate (BioFx). For the determination of immune complex and immune complex formation, after capture, plates were washed in PBS and 100 μl of affinity purified IMP labeled sheep anti-human IgG antibody (1:2500 in blocking buffer) was added. After incubation for 1 hour at 37° C. the antiserum was aspirated and the plates washed 4×300 ul PBSTA. Bound HRP was detected with tetramethylbenzidine (TMB) (BioFx).

FIG. 4 shows that GNA agarose removed gp120 from buffer solution with 99% efficiency in <1.5 minutes. Because gp120 is a heavily glycosylated protein which can bind non-specifically to a variety of surfaces, it is not surprising that the control column also bound 85% of the input gp120.

Example 7

This Example demonstrates the removal of HIV gp120 from infected plasma using a lectin affinity plasmapheresis device. The plasmapheresis device described in Example 4 was equilibrated with 5-10 column volumes sterile PBS. A plasma sample of about 1.5 ml containing gp120 (typically 500 ng/ml) was circulated over the column at a flow rate of 0.5-0.6 ml/min at room temperature. The circulating solution was tested at various time intervals for the presence of gp120 and gp120 immune complexes where appropriate as in Example 6.

Since anti-gp120 antibodies are typically abundant in HIV+ plasma, removal of gp120 from infected plasma might be expected to be more difficult than removal from simple buffer solutions. In part due to these antibodies, gp120 detection in HIV+ plasma and blood typically shows at best low amounts of gp120. In order to measure removal it was therefore necessary to add gp120 to infected patient plasma to provide a sample for measurement. ELISA measurement of the sample confirmed that all of the added gp120 in this sample was complexed with anti-gp120 antibodies (data not shown).

Figure 5:
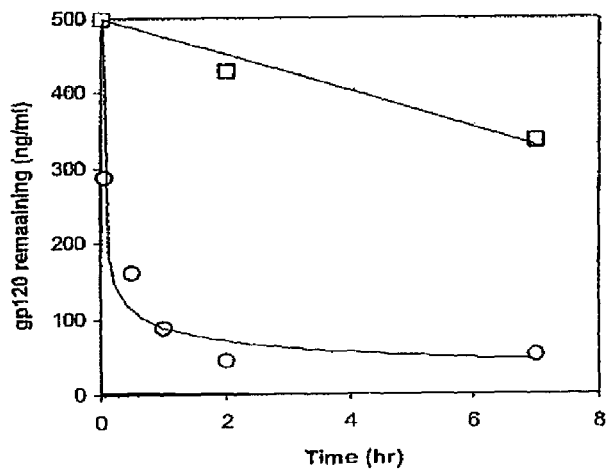
FIG. 5 is a graphical representation of the removal of gp120 immune complexes from HIV infected human plasma. Initial gp120 was 500 ng/ml in human HIV+ plasma (1.6 ml/run). Assayed with 10 µg/well GNA/NPA plate to capture gp120 immune complexes detected with sheep anti-human IgG. Plasma was recirculated over a Glen Research column containing 0.2 ml GNA agarose vs Sepharose 4B control at 0.5-0.58 ml/min and room temperature. Lines are theoretical exponential best-fit $R^2=0.91$ for Experimental (O) and linear for Control (□).

FIG. 5 shows that the GNA agarose affinity resin effectively removed gp120 in immune complexes from HIV infected plasma samples. Removal was rapid with an apparent half reaction time of 20 minutes. A portion of the gp120 signal was not removed (~10% of the initial gp120 immune complex) even after 7 hours and appeared to represent background binding of IgG in the assay.

Example 8

This Example demonstrates removal of HIV virions from infected plasma using GNA plasmapheresis. An HIV infected plasma sample (ER8-03030-0002 native HIV, Boston Biomedica, Boston Mass.) containing 100,000 copies per ml (cpm) of the virus was circulated over a 0.2 ml GNA agarose column described in Example 4. At intervals, 250 μl aliquots of the plasma were taken and the viral RNA extracted using TRI-LS reagent according to, the manufacturers instructions (MRC Corporation). HIV viral RNA was then quantitated using real time RT PCR and an Access 1 step reagent set from Promega (Madison, Wis.) in 25 μl reaction volumes containing 400 nM SK432 and SK461 gag gene primers, Sybr green (1:10,000), 1×SCA blocking buffer, 3 mM $MgCl_2$, 400 uM dNTPs and 10 ul of unknown RNA or HIV-1 RNA from armored RNA standards (Ambion Austin Tex.). Amplification and reaction times were: RT (45 minutes at 48° C.) and PCR 40 cycles (94° C./15 sec; 62° C./30 sec; 72° C./60 sec; 83° C./read) in a SmartCycler real time thermocycler (Cepheid, Sunnyvale, Calif.) essentially according to the manufacturers instructions. When necessary for confirmation of amplification, 10 μl aliquots of the amplification mix were subjected to agarose gel electrophoresis 2% (w/v) (Sigma, molecular biology grade) in 0.5× TBE buffer pH 8.3 containing 0.25 ug/ml ethidium bromide for 45 minutes at 120 VDC at room temperature. Gels were photographed on a UV transilluminator with the images subsequently digitized and analyzed using ImageJ.

Figure 6A:
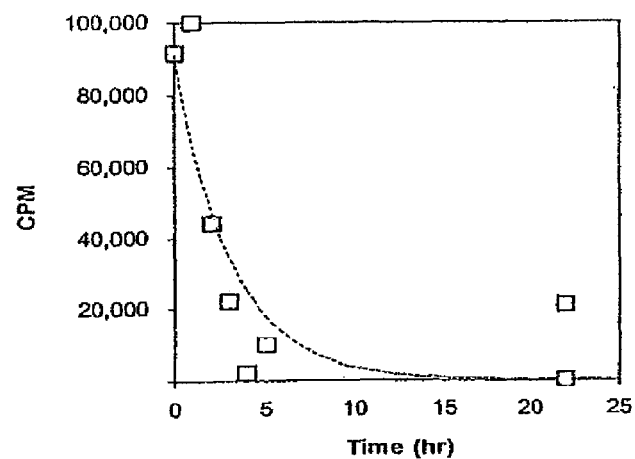
FIGS. 6A and 6B demonstrate the removal of native HIV on GNA Agarose
Figure 6B:
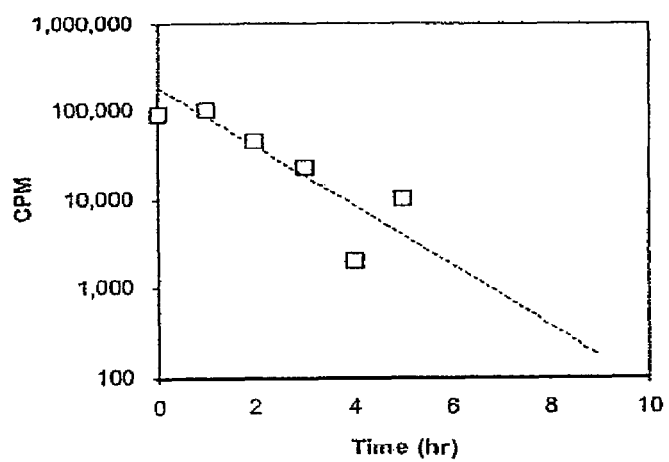

FIGS. 6A and 6B show that GNA agarose effectively removes HIV virions from infected plasma. FIG. 6A is a linear plot of the data curve fit to a exponential decay ($R^2$=0.9). The curve predicts essentially quantitative removal of HIV in about 10 hours. FIG. 6B is a log plot of the HIV removal rate which gives an estimate of 0.9 hours as the half time of HIV removal. Virus removal appears first order as expected for GNA in excess over virus. CPM indicates HIV copies/ml.

Example 9

This Example demonstrates removal of gp120 from HIV infected blood using a GNA lectin affinity hemodialysis device. Since most HIV+ plasma samples have low or undetectable amounts of gp120, simulated HIV infected blood samples were prepared by mixing 5 ml type O+ fresh packed red cells with 5 ml HIV infected plasma (typically $10^5$ cpm) to which was added sufficient gp120 IIIB to make the sample 100 ng/ml The affinity hemodialysis devices described in Example 5 were equilibrated with 5-10 column volumes sterile PBS. A control column containing only Sepharose 4B was prepared as a control. The infected blood sample ~10 ml containing gp120 was recirculated over the column at a flow rate of 0.9 ml/min at 37° C. using a Masterflex roller pump (1 rpm) and Pharmed 6485-16 silicon tubing. The circulating solution was tested at various time intervals for the presence of free gp120 after acid denaturation and neutralization to disrupt immune complexes.

Figure 7:
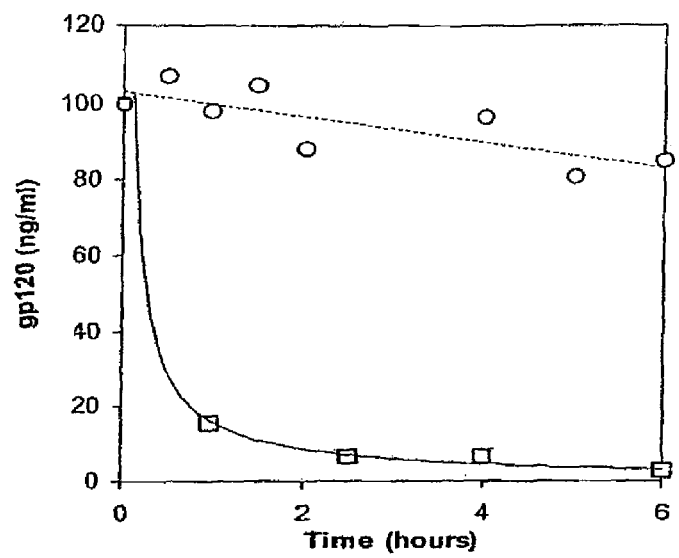
FIG. 7 is a graphical representation of the removal of gp120 from HIV+ blood. Initial gp120 was 100 ng/ml in human HIV+ plasma. Assayed with 0.1 ug/well GNA-NPA plate with immune complexes disrupted with acid/detergent prior to assay. The blood was recirculated over a Microkros column containing 0.6 ml GNA agarose vs. Sepharose 4B control. Flow rate 0.9 ml/min at 37° C. using a Masterflex pump (1 rpm) and Pharmed 6485-16 tubing. Lines are theoretical exponential best-fit $R^2=0.91$ for Experimental (□) ($t_{1/2}=22$ min) and linear for Control (O).

FIG. 7 shows that as the blood samples were recirculated over the cartridge, the initial gp120 of 100 ng/ml was reduced to background levels in 4 to 6 hours (apparent $t_{1/2}$=22 min). The control cartridge removed gp120 very slowly.

Example 10

This example demonstrate removal of HCV from infected blood using GNA lectin affinity hemodialysis. In order to show the broad specificity of GNA lectin removal of viruses, we performed lectin affinity hemodialysis on HCV infected blood. The lectin affinity hemodialysis devices described in Example 4 were equilibrated with 5-10 column volumes sterile. PBS. HCV infected blood samples were prepared by mixing 1 ml type O+ fresh packed red cells with 1 ml HIV infected plasma (typically $10^5$ cpm). The infected blood sample was recirculated over the column at a flow rate of 0.5 ml/min at room temperature using a Masterflex roller pump (1 rpm) and Pharmed 6485-16 tubing. The circulating solution was tested at various time intervals for the presence HCV viral RNA.

Viral RNA was isolated using TRI-LS (MRC Corporation) from 100 µl of plasma according to the manufacturers instructions. HCV viral RNA was then measured by quantitative RT PCR performed using an ImpromII reagent set from Promega (Madison, Wis.) in 25 ul reaction volumes containing 400 nM EY80 and EY78 HCV specific primers, Sybr green (1:10,000), 1×SCA blocking buffer, 3 mM $MgCl_2$, 400 uM dNTPs, 0.2 units/ul each of Tfl polymerase and AMV reverse transcriptase. Typically 50 ul of the mix was used to dissolve RNA isolated from 100 µl plasma and the mix split into two identical duplicate samples. Amplification and reaction times were: RT (45 minutes at 48° C.) and PCR 40 cycles (94° C./15 sec; 62° C./30 sec; 72° C./60 sec; 87° C. readout) in a SmartCycler real time thermocycler (Cepheid, Calif.) essentially according to the manufacturers instructions. The amount of viral RNA was estimated by comparison to the signal strength of the viral RNA standards in the initial phase of the amplification reaction ($C_t$=20).

Figure 8:
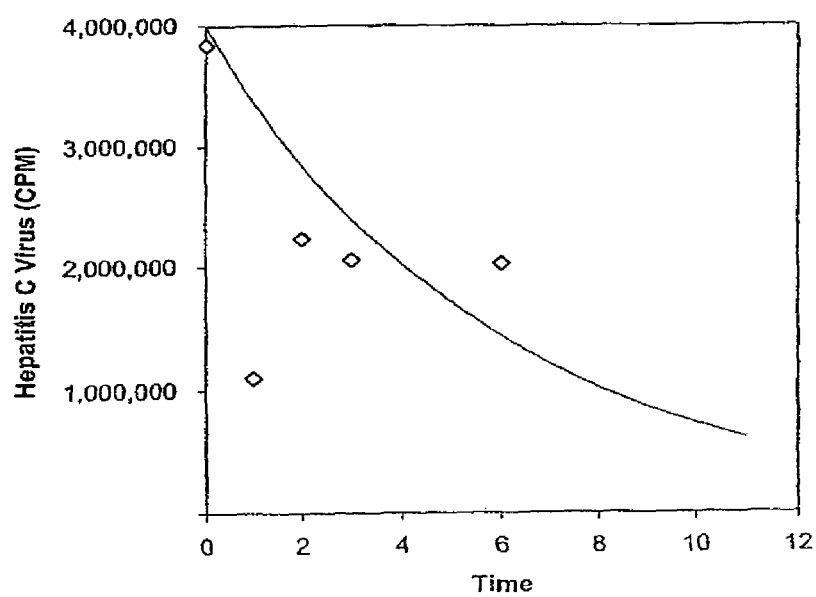
FIG. 8 is a graphical representation of the removal of Hepatitis C virus infected blood. The blood was recirculated over a Microkros column containing 0.6 ml GNA agarose vs. Sepharose 4B control. Flow rate 0.5 ml/min at room temperature using a Masterflex pump (1 rpm) and Pharmed 6485-16 tubing. The line is a theoretical exponential best-fit $R^2=0.85$.

FIG. 8 shows that as the blood was recirculated over the cartridge, the initial HCV was reduced about 50% in 3 hours (apparent $t_{1/2}$=3 hours). The curve fit reasonably well to an exponential decay.

From the foregoing, it will be obvious to those skilled in the art the various modifications in the above-described methods, and compositions can be made without departing from the spirit and scope of the invention. Accordingly, the invention may be embodied in other specific forms without departing from the spirit or essential characteristics thereof. Present examples and embodiments, therefore, are to be considered in all respects as illustrative and not restrictive, and all changes which come within the meaning and range of equivalency of the claims are therefore intended to be embraced therein.

I claim:

1. A lectin affinity hemodialysis cartridge, comprising:
   a filtration chamber configured to receive blood or plasma contaminated with viral particles;
   a lectin covalently coupled to agarose or to aminocelite disposed within said filtration chamber; and
   a porous hollow fiber membrane, wherein said membrane has pores of 200-500 nm in diameter;
   wherein the lectin is selected from the group consisting of: *Galanthus nivalis* agglutinin (GNA), *Narcissus pseudonarcissus* agglutinin (NPA), cyanovirin, and Conconavalin A, and mixtures thereof
   wherein the cartridge is configured to remove said viral particles from the blood or plasma.

2. The lectin affinity hemodialysis cartridge of claim 1, wherein said filtration chamber further comprises an inlet port and an outlet port;
   wherein a channel of said hollow fiber membrane is in fluidic communication with said inlet and said outlet ports;
   said cartridge having an extrachannel space within said chamber which surrounds said hollow fiber membrane; and
   wherein said lectin is covalently coupled to agarose or to aminocelite that is disposed within said extrachannel space proximate to an exterior surface of said membrane.

3. The lectin affinity hemodialysis cartridge of claim 1, wherein said membrane has an inside diameter of about 0.3 mm and an outside diameter of about 0.5 mm.

4. The lectin affinity hemodialysis cartridge of claim 1, wherein the cartridge is configured to remove greater than about 50% of viral particles present in the blood or plasma.

5. The lectin affinity hemodialysis cartridge of claim 1, wherein the cartridge is configured to remove greater than about 90% of viral particles in the blood or plasma.

* * * * *